# United States Patent

Harada et al.

[11] Patent Number: 4,640,251
[45] Date of Patent: Feb. 3, 1987

[54] METHOD OF DISCRIMINATING OCTANE NUMBER OF FUEL FOR MOTOR VEHICLE

[75] Inventors: Osamu Harada; Toshio Suematsu; Yuji Takeda; Katsushi Anzai, all of Toyota, Japan

[73] Assignee: Toyota Jidosha Kabushiki Kaisha, Japan

[21] Appl. No.: 775,431

[22] Filed: Sep. 12, 1985

[30] Foreign Application Priority Data

Oct. 1, 1984 [JP] Japan ................................ 59-206031

[51] Int. Cl.$^4$ .................... G01N 33/22; F02D 43/00
[52] U.S. Cl. .................................. 123/425; 123/422; 123/435; 123/492; 73/35
[58] Field of Search .............. 123/425, 435, 422, 492; 73/35

[56] References Cited

U.S. PATENT DOCUMENTS

4,513,716  4/1985  Haraguchi et al. ............... 123/425

FOREIGN PATENT DOCUMENTS

58-143169  8/1983  Japan ............................. 123/425

*Primary Examiner*—Andrew M. Dolinar
*Attorney, Agent, or Firm*—Finnegan, Henderson, Farabow, Garrett & Dunner

[57] ABSTRACT

A knocking in an engine is prevented from occurring by retarding an ignition timing. A basic ignition advance angle THB and a correction value THK for retardation of the ignition timing are computed in order that the ignition timing THF is calculated by using the following formula.

$$THF = THB - THK$$

The knocking in the engine tends to take place, as the ignition timing advances. Determination is made as to whether the correction value THK is equal to a reference value or not and detection is made as to whether a rapid acceleration takes place. If the result of such determination is affirmative and no rapid acceleration is detected, discrimination is made as to whether an octane number of the fuel to be supplied to the engine is less than a predetermined octane number of the fuel which is optimum for the engine. When rapid acceleration is detected, the above-mentioned discrimination is not carried out so that the engine is controlled by the previous result of the discrimination of the fuel.

10 Claims, 14 Drawing Figures

METHOD OF DISCRIMINATING OCTANE NUMBER OF FUEL FOR MOTOR VEHICLE

BACKGROUND OF THE INVENTION

The present invention relates to a method of discriminating a type of a fuel to be supplied to an engine of a motor vehicle. More particularly, the present invention relates to a method of discriminating an octane number of a fuel. In other words, in the present invention, determination is made as to whether the gasoline has a high-octane number or a low-octane number.

It is well known to control an ignition timing at which an ignition plug sparks in accordance with an engine rotational speed and an engine load as well as an occurrence of a knocking of the engine. In this case, when the knocking is detected the ignition timing is retarded or approached the side of the top dead center of the crank shaft of the engine.

You can access two types of gasolines, i.e., the high-octane gasoline and the low octane gasoline. In this specification, the term of the low-octane gasoline means that an octane number of the low-octane gasoline is less than that of the high-octane gasoline. On the other hand, two types of gasoline engines optimum for the high-octane gasoline and the low-octane gasoline, respectively, are available for the consumer. It is well known that a maximum performance of the engine is achieved when the ignition advance angle is advanced to a critical ignition advance angle relating to the knocking of the engine. In case the ignition advance angle is advanced beyond the critical ignition advance angle, the engine would knock.

It is also well known that the more the octane number of the gasoline gets, the more the critical ignition advance angle can get.

In this connection, the following problems may be raised. In case the low-octane gasoline is supplied to the gasoline engine (referred to as "an engine for high octane gasoline" hereinafter) designed suitably for the high-octane gasoline, the knocking of the engine would frequently occur since an ignition plug may be ignited at the ignition advance angle more than an optimum or critical ignition advance angle for the low-octane gasoline. In case the high-octane gasoline is supplied to the gasoline engine (referred to as "an engine for low-octane gasoline" hereinafter) designed suitably for the low-octane gasoline, a maximum performance of the engine, which is achieved when the low-octane gasoline is used, may not be expected to be obtainable. This is because the ignition plug may be ignited at the ignition advance angle which is retarded too much with respect to the critical ignition advance angle. More specifically, by supplying the high-octane gasoline to the engine for low-octane gasoline, the ignition advance angle could be advanced to the critical ignition advance angle for the high-octane gasoline so that an output torque of the gasoline engine increases and an exhaust gas temperature decreases resulting in decrease of a fuel injection rate. However, since the gasoline engine for low-octane gasoline provides the ignition advance angle optimum for low-octane gasoline, no critical ignition advance angle for high-octane gasoline is obtainable. This causes the above-mentioned disadvantage.

In order to obviate these disadvantages, there has been proposed in Japanese Patent Application laid-open No. 57072/1983 an apparatus for controlling an ignition timing in which two tables of ignition timings for high and low octane gasoline are prestored and one of the tables is selected by a driver's switching operation of a switch for selecting of the table. Such a switch may be provided on an instrument panel of the motor vehicle. This apparatus, however, is subjected to the following problem. An erroneous switching operation of the switch for selection of the above table causes the same advantages mentioned above. This is because the driver has to determine which one of high and low-octane gasolines is supplied to the engine so that one of the tables of the ignition timing is selected by switching operation of the switch.

Further, there has been proposed in Japanese Patent Application laid-open No. 231980/83 an apparatus for controlling an ignition timing in which determination as to the type of the gasoline to be supplied to the engine is carried out in accordance with a knocking condition of the engine. However, the proposed apparatus necessitates an additional ignition advance angle map for discrimination of the type of the gasoline to be supplied together with a well-known ignition advance angle map for general control of the ignition timing based on an engine operational condition. In discriminating the type of the gasoline to be supplied, the ignition advance angle is selected from the additional ignition advance angle map, at first, and then the ignition plug sparks at the ignition advance angle thus selected. Thereafter determination is made as to whether the knocking of the engine takes place or not. If it is determined that the knocking of the engine takes place, it is found that an undesirable gasoline, e.g., low-octane gasoline is used. Such sequential procedures of discrimination of the gasoline requires a relatively longer period of time. In addition, in case no additional ignition advance angle map is provided, the ignition advance angle for discrimination of the type of the gasoline has to be calculated from the ignition advance angle for general control of the ignition timing based on the engine operational condition.

Furthermore, it is well known that the engine tends to knock under a rapid acceleration of the engine regardless of the types of the gasoline used. If the detection of the knocking of the engine due to the rapid acceleration is used in order that discrimination of the type of the gasoline is made, such a discrimination may become inaccurate.

SUMMARY OF THE INVENTION

It is an object of the present invention to provide a method of discriminating a type of a fuel for motor vehicle obviating the above-mentioned disadvantages.

The method according to the present invention is applicable to an internal combustion engine in which a basic ignition advance angle is determined on the basis of an engine rotational speed and an engine load and retarded in accordance with a knocking of the engine greater than a first reference level of the knocking intensity. It is preferable to calculate a correction value for retardation of the basic ignition advance angle and retard the basic ignition advance angle by the correction value thus calculated. The correction value increases by a predetermined value every time the knocking greater than the first reference level is detected until it reaches a maximum value. The basic ignition advance angle is predetermined in such a manner that the engine runs with a maximum performance thereof when a gasoline having a specific octane number, e.g., a high-octane gasoline, is used. The correction value increases to the maximum value when the knocking of the engine takes place frequently due to, for example, usage of a gasoline having an octane number less than the specific octane number, e.g., a low-octane gasoline. In case the correction value is increased to the maximum value and still the knocking takes place the knocking would not be prevented from occuring. Besides, a heavy knocking would take place, in case a fuel tank of the engine for the high octane gasoline is filled with the low-octane gasoline. Accordingly, in accordance with a frequency of occurrence of the heavy knocking during the correction value being maximum value, discrimination can be made as to whether or not the gasoline having the specific octane number is supplied to the engine.

According to a first aspect of the present invention, determination is made as to whether the correction value for retardation of the ignition timing is equal to a predetermined value and detection is made as to whether a rapid acceleration takes place. Further, detection is made as to whether the knocking of the engine takes place and the knocking intensity is compared with the first reference level and a second reference level greater than the first level. When the knocking is greater than the first reference level, the correction value is increased. As for the second reference level, if no rapid acceleration is detected, the frequency of occurrence of the knocking greater than the second reference level (referred to as "heavy knocking") is measured. If the frequency of occurrence of the heavy knocking is greater than a first reference frequency, it is determined that the low-octane gasoline is used. In short, detection of the rapid acceleration inhabits discrimination of the type of the fuel.

According to a second aspect of the present invention, even if the rapid acceleration is detected, discrimination of the type of the fuel is carried out in which the first reference frequency of occurrence of the heavy knocking is changed to a second reference frequency greater than the first reference frequency.

The present invention is advantageous in that discrimination of the type of the fuel is made in accordance with the knocking caused only by usage of an undesirable gasoline having a low-octane number and an erroneous discrimination of the type of the fuel is prevented from occurring.

DESCRIPTION OF THE PREFERRED EMBODIMENT

Figure 1:
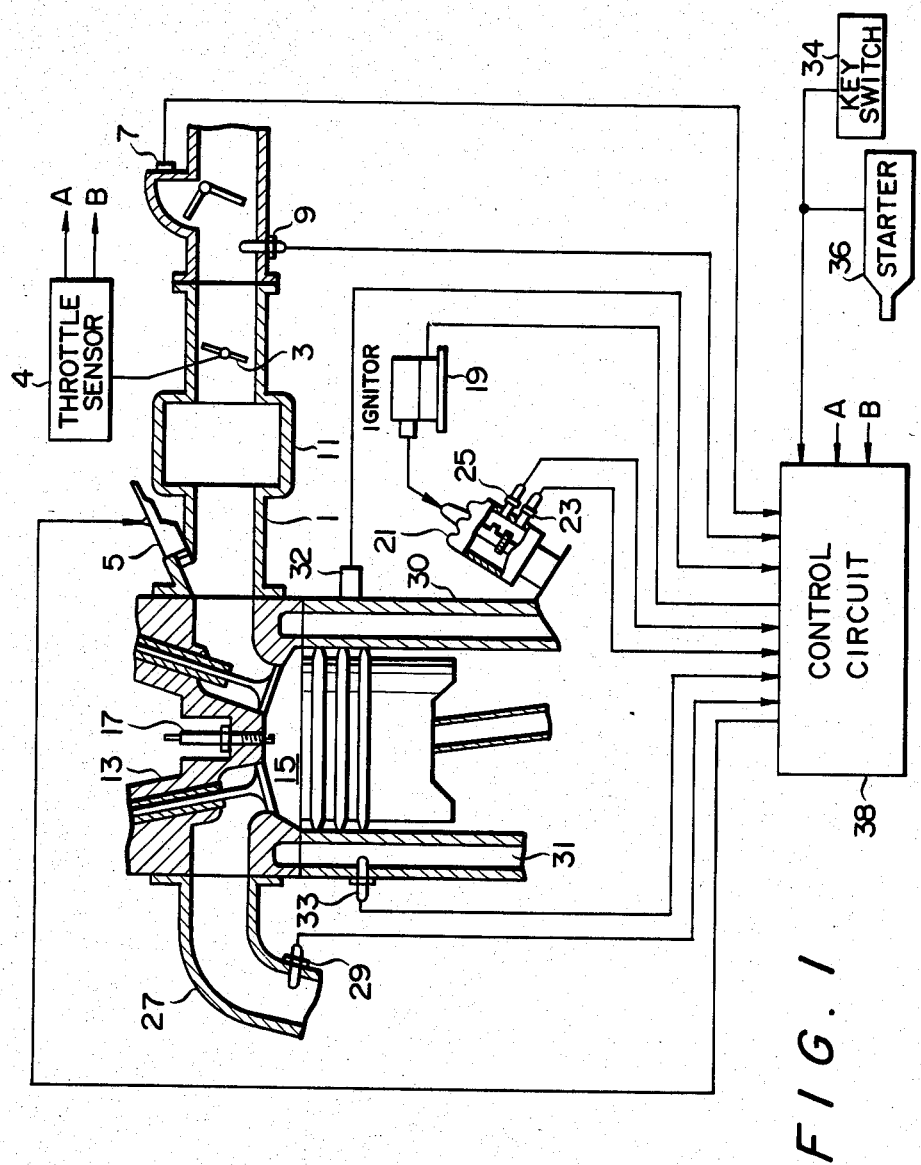
FIG. 1 is a schematic illustration of one example of an engine to which the method according to the present invention is applicable.
Figure 2:
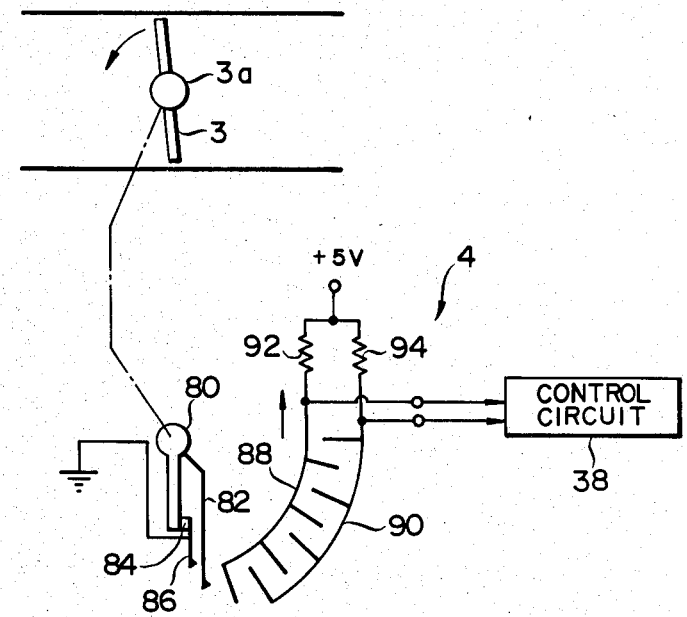
FIG. 2 is a schematic illustration of one example of a throttle sensor shown in FIG. 1.

Referring to FIG. 1, fuel injectors 5 are provided in an intake pipe 1 at a downstream portion of a throttle valve 3. An intake air quantity is dependent on an open degree of the throttle valve 3 and is measured by an air flow meter 7 which outputs a signal depending upon the intake air quantity. Provided at the downstream portion of the air flow meter 7 is an intake air temperature sensor 9 outputting a signal depending upon an intake air temperature. A surge tank 11 is provided at a downstream portion of the throttle valve 3. A throttle sensor 4, which is shown in detail in FIG. 2, is connected with an axle of the throttle valve 3. An output of the throttle sensor 4 is connected to an electronic control circuit 38 described hereinafter so that a rapid acceleration of the engine is detected. Reference numeral 13 is a conventional internal combustion engine whose ignition plugs 17 spark so as to ignite an air-fuel mixture in a combustion chamber 15 at a certain ignition advance angle prior to the top dead center of each cylinder. Each ignition plug 17 is applied with a high voltage increased by an ignitor 19 through a distributor 21.

The distributor 21 is provided with a crank angle sensor 23 generating a pulse signal every 30 degree of a rotational angle of a crank shaft (referred to as "30° CA" hereinafter) and a cylinder discriminating sensor 25 generating a pulse signal every 720° (CA).

An exhaust gas produced after combustion in the combustion chamber is exhausted via an exhaust pipe 27 where an $O_2$ sensor 29 generating a signal which depends on the concentration of the oxygen remaining in the exhaust gas, is provided. A water temperature sensor 33 is installed at a cylinder block 30 so as to sense a cooling water temperature in a water jacket 31 so that the sensor 33 generates a voltage corresponding to the cooling water temperature. A knocking sensor 32 is also installed at the cylinder block 30 which generates a signal depending on a magnitude of the knocking of the engine. The knocking sensor 32 may be a resonant type vibration sensor which outputs a maximum output in response to a predetermined frequency of vibration of the engine. Further, denoted at 34 and 36 are a key switch and a starter, respectively. Turning on of the key switch 34 causes the starter 36 to be driven and both ignition and fuel injection systems to be enabled. Denoted at 38 is an electronic control circuit whose input port receives a plurality of signals from the sensors, switches and so on.

Referring to FIG. 2, explanation will be given of the throttle sensor 4 hereinbelow.

As shown in FIG. 2, the throttle sensor 4 is provided with a L-shaped rotary piece 80 whose end portion is connected with the axle 3a of the throttle valve 3. One end of a first contact piece 82 is rotatably secured to a base of the rotary piece 80 such that the first contact piece 82 extends along the rotary piece 80 without contact therewith. One end of a second contact piece 86 is secured through an insulator 84 to a top portion of the rotary piece 80 such that the second contact piece 86 is parallel to the first contact piece 82. The second contact piece 86 is grounded. Comb-shaped first and second electrodes 88 and 90 are arranged such that respective teeth of the one electrode is positioned between respective teeth of the other electrode. The first and second electrodes 88 and 90 are connected to a power supply through registers 92 and 94, respectively, and to the electronic control circuit 38.

Figure 3:
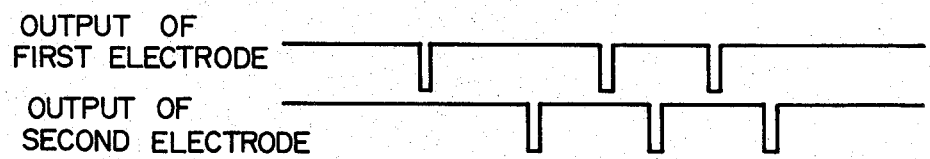
FIG. 3 is a time chart of outputs from the throttle sensor.

The rotary piece 80 rotates together with the throttle valve 3. When the throttle valve 3 rotates to open, under the condition that the first and second contact pieces 82 and 86 are in contact with each other, the top portion of the first contact piece 82 is in contact with the first and second electrodes 88 and 90 alternatingly. Consequently, the throttle sensor 4 outputs a pulse signal as shown in FIG. 3. On the contrary thereto, when the throttle valve 3 rotates to close, the first contact piece 82 is delayed to be rotated behind the second contact piece 86. Therefore, no pulse signal is generated.

Figure 4:
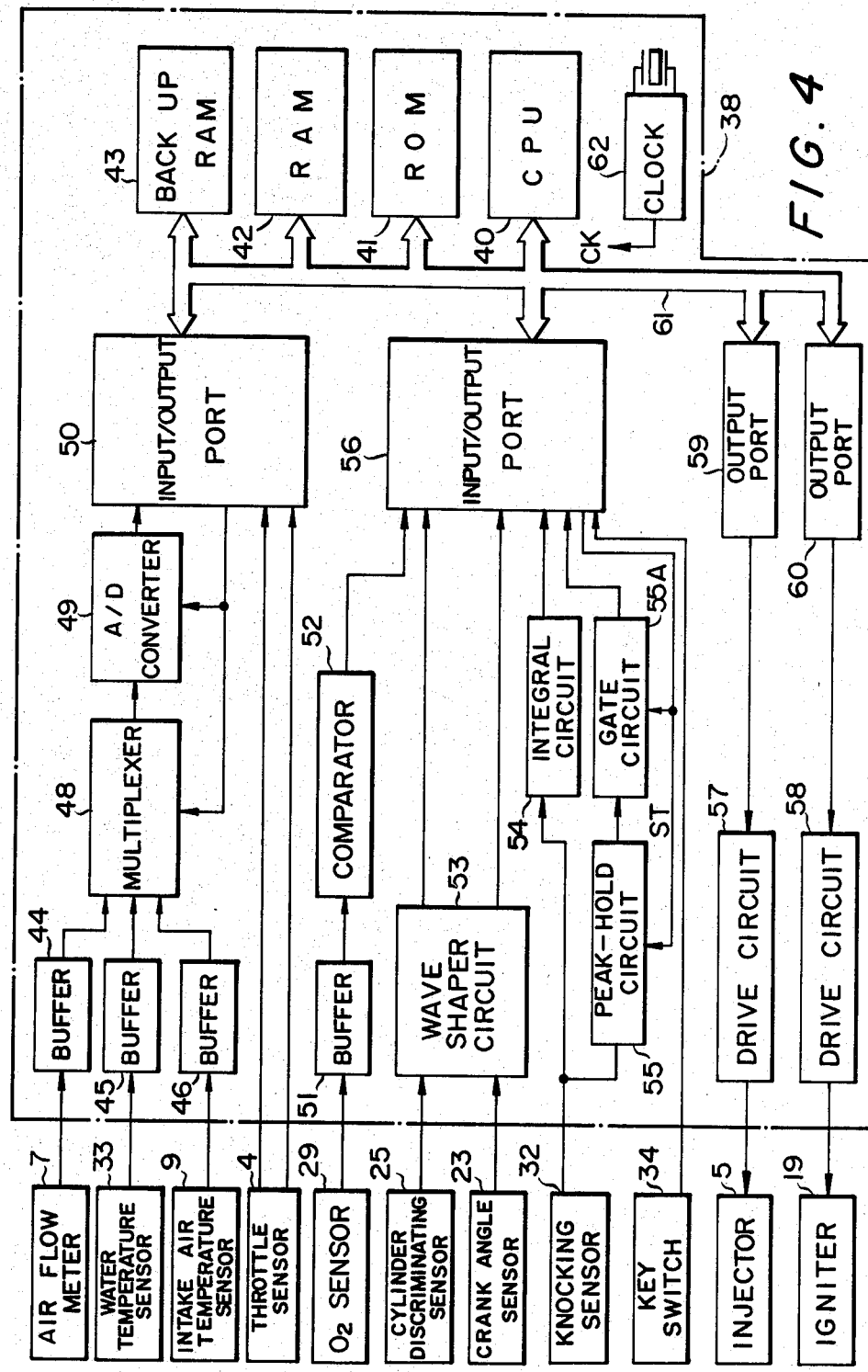
FIG. 4 is a detailed block diagram of an electronic control circuit of the engine shown in FIG. 1.

Referring to FIG. 4, description will be given of the electronic control circuit 38. Denoted at 40 is a central processing unit (CPU) controlling various components so as to successively receive input signals from the sensors, switches and so on, and to carry out a logical and arithmetic operation in accordance with various programes prestored in a read only memory (ROM) 41 which also prestores initial data. Denoted at 42 is a random access memory (RAM) 42 in which various data received by the control circuit 38 and required for logical and arithmetic operation are temporarily written and read out. A back-up memory (BU-RAM) 43 is supplied with electricity from an auxiliary power source, e.g. a battery when the engine is out of operation, in order to maintain various data required for optimum restarting condition of the engine. Reference numerals 44-46 are buffers for output signals from respective sensors and 48 is a multiplexer successively selecting one of these output signals so as to feed the signal thus selected to the CPU 40. Reference numeral 49 is an analogue-to-digital converter converting the analogue signals into digital signals and 50 an input and output port through which each digital signal from the A/D converter 49 is fed to CPU 40 and a control signal from CPU 40 is fed to the A/D converter 49 and the multiplexer 48. Denoted at 51 is a buffer through which the output signal from the O$_2$ sensor 29 is fed to a comparator 52. Denoted at 53 is a wave shape circuit shaping the waves of the output signals from the crank angle sensor 23 and the cylinder discriminating sensor 25.

The output of the knocking sensor 32 is fed to an integral circuit 54 and a peak-hold circuit 55 whose output is fed to an input and output port 56 through a gate circuit 55A. In general, the knocking of the engine occurs within a range from 30° (CA) to 60° (CA) after the top dead center (TDC) of the crank shaft. A timing signal ST which is fed to the gate circuit 55A and the peak-hold circuit 55 through the input and output port 56, therefore, is generated so that a peak value out of the successive outputs of the knocking sensor 32 is taken in within the above range of the rotatonal angle of the crank shaft.

Figure 5:
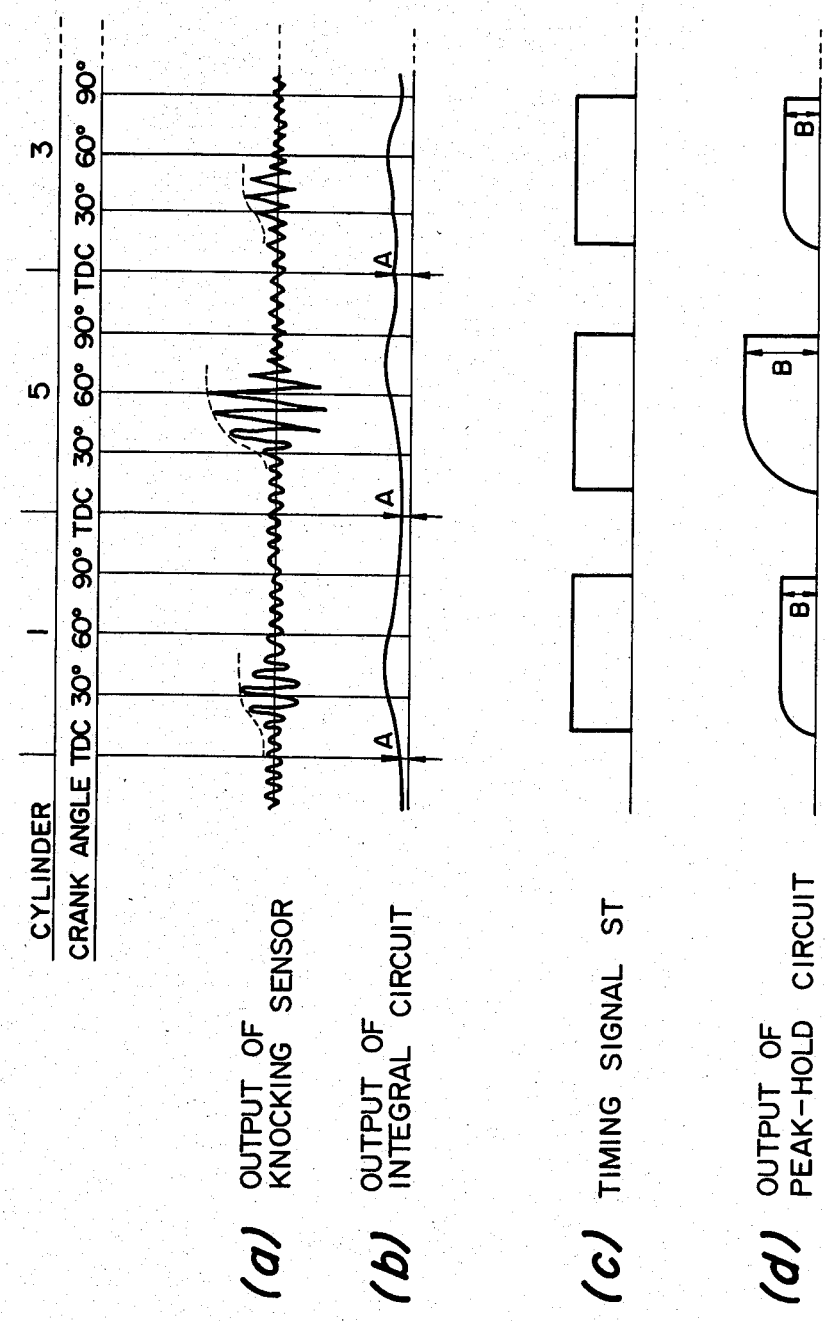
FIGS. 5 (a)-5(d) are time charts showing output signals from each of elements of a knocking detecting means.

FIG. 5 shows the output signals from the knocking sensor 32, the integral circuit 54 and the peak-hold circuit 55 as well as the timing signal ST for 6-cylinder gasoline engine. A firing order of the cylinder and the crank shaft rotational angle after the top dead center of each cylinder are indicated along an abscissa of the drawing of FIG. 5. A wave form (a) is indicative of the output of the knocking sensor 32, (b) the output of the integral circuit 54, (c) the timing signal ST and (d) the output of the peak-hold circuit 55. The peak-hold circuit is adapted to be enabled by the leading edge of the timing signal ST and disabled by the trailing edge of the timing signal ST, and the output signal of the peak-hold circuit 55 is adapted to be passed through the gate circuit 55A receiving the timing signal ST being of high level. In this embodiment, the output of the integral circuit 54 at the top dead center of the crank shaft is adapted to be taken in as a background level A and the output thereof at the 90° (CA) after the top dead center of the crank shaft is adapted to be taken in as a knocking signal B.

Referring again to FIG. 4, reference numerals 57 and 58 are drive circuits driving the fuel injectors 5 and the ignitor 19, respectively, by each of signals from CPU 40 via output ports 59 and 60. Denoted at 61 is a bus line for various signals and data and 62 a clock circuit feeding a clock pulse signal at a constant time interval to the CPU 40, ROM 41, RAM 42 and so on.

I. Gasoline Engine Designed for High-octane Gasoline

The following description will be given of sequential procedures for discriminating the type of the gasoline to be supplied to the engine designed for high-octane gasoline. An ignition control and a fuel injection control are carried out according to a result of such a discrimination.

Main Routine

Figure 6:
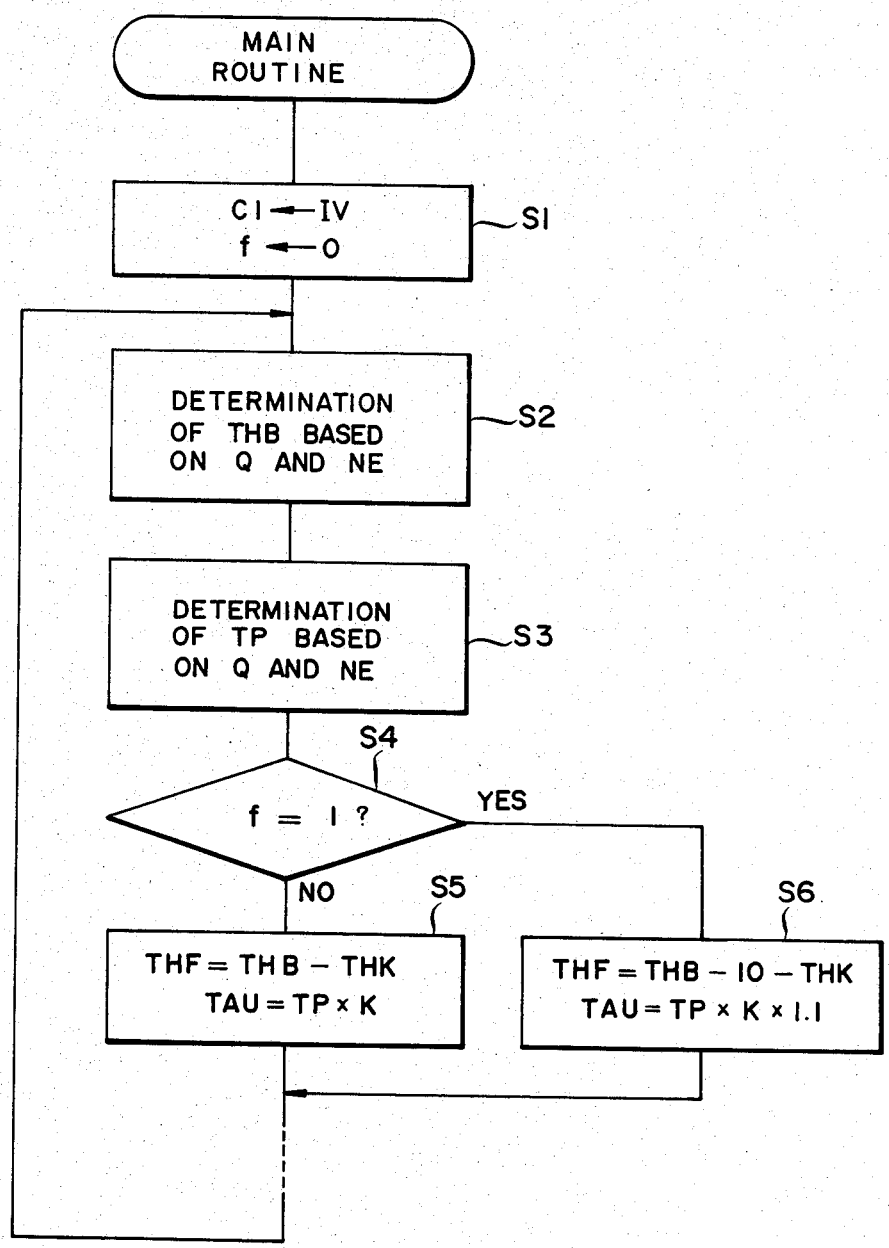
FIGS. 6 is a flow chart of one example of main routine.

FIG. 6 shows a main routine starting in response to turning on of the key switch 34. In a step S1, a counter which counts the number of ignitions between two successive detections of a heavy knocking, is initialized so that a content C1 of the counter becomes an initial value IV and a flag f representing the result of discrimination of the type of the gasoline is set to be "0". The main routine is preprogrammed such that the step S1 is carried out only when the key switch 34 is turned on in order to drive the starter 36 and thereafter the step S1 is skipped over. Consequently, the step S1 is carried out again when the key switch 34 is operated again in order to drive the starter after turning off the key switch 34.

In a step S2, a basic ignition advance angle THB is determined in accordance with a relationship between an air flow quantity Q and an engine rotational speed NE. It may be possible to prestore in the ROM 41 a table for basic ignition advance angle THB with respect to relationship between the air flow quantity Q obtained on the basis of the voltage signal from the air-flow meter 7 and the engine rotational speed NE obtained on the basis of the pulse signal from the sensor 23. A process goes to a step S3 in which a basic fuel injection time duration TP is determined in accordance with a relationship between the air flow quantity Q and the engine rotational speed NE. Like the basic ignition advance angle THB, it is preferable to prestore a table for the fuel injection time duration TP with respect to the relationship between the air flow quantity Q and the engine rotational speed NE. In a step S4, determination is made as to whether the flag f is "1" or not. The flag f is used in order that discrimination is made as to whether the gasoline to be supplied to the engine is high-octane gasoline or low-octane gasoline. The flag f is set to be "1" when it is determined that the low-octane gasoline is used in a fuel discriminating routine described hereinafter. That is, flag f "1" is indicative of use of the low octane gasoline and the flag f "0" is indicative of use of the high-octane gasoline in this embodiment. More specifically, when the octane number of the gasoline in the fuel tank of the engine is less than an allowable certain octane number, the flag f is set to be "1" due to a frequent occurrence of the heavy knocking. The allowable octane number may be less than the octane number of the high-octane gasoline. If the octane number of the gasoline in the fuel tank in which the low-octane gasoline is mixed with the high-octane gasoline is greater than the allowable octane number, it is scarcely possible that the heavy knocking takes place, resulting in flag f being "0".

If the step S4 is determined to be negative, the process proceeds to a step S5 wherein the following formulas are calculated.

$$THF = TH - THK \quad (1)$$

$$TAU = TP \times K \quad (2)$$

If the step S4 is determined to be affirmative, the process goes to a step S6 wherein the following formulas are calculated.

$$THF = THB - 10° (CA) - THK \quad (3)$$

$$TAU = TP \times K \times 1.1 \quad (4)$$

where,
THF: final injection advance angle
THB: basic injection advance angle for gasoline engine designed suitably for the high-octane gasoline
THK: correction value for retardation in response to occurrence of the knocking of the engine
TAU: final fuel injection time duration
TP: basic fuel injection time duration
K: correction coefficient for a water temperature, an engine operational condition and so on In addition, the correction value THK is limited to a maximum value THK mx so that the exhaust gas temperature increased due to retardation of the ignition timing is prevented from exceeding a temperature allowable for the engine. The above formula (3) is used when it is determined in the fuel discriminating routine described hereinafter that the low-octane gasoline is supplied, i.e., the octane number of the gasoline in the fuel tank is less than the allowable octane ununber. According to the formula (3), the final ignition advance angle THF is retarded by 10° (CA) with respect to the final ignition advance angle THF obtained by using formula (1). This is because the engine tends to knock due to the low-octane gasoline. As shown in the formula (4), the final fuel injection time duration TAU is increased by ten percent over the same obtained by the formula (2), so that the exhaust gas temperature increased and the output torque decreased due to such a retardation of the ignition timing are compensated.

In a particular embodiment shown in FIG. 6, the process is adapted to proceed to the step S2 after the step S5 or S6 has been carried out. The ignition and the fuel injection are conventionally controlled in accordance with the final ignition advance angle THF and the final fuel injection time duration TAU, respectively. The detailed procedures of such controls, therefore, are omitted in this specification.

Knocking Detection Routine

Figure 7:
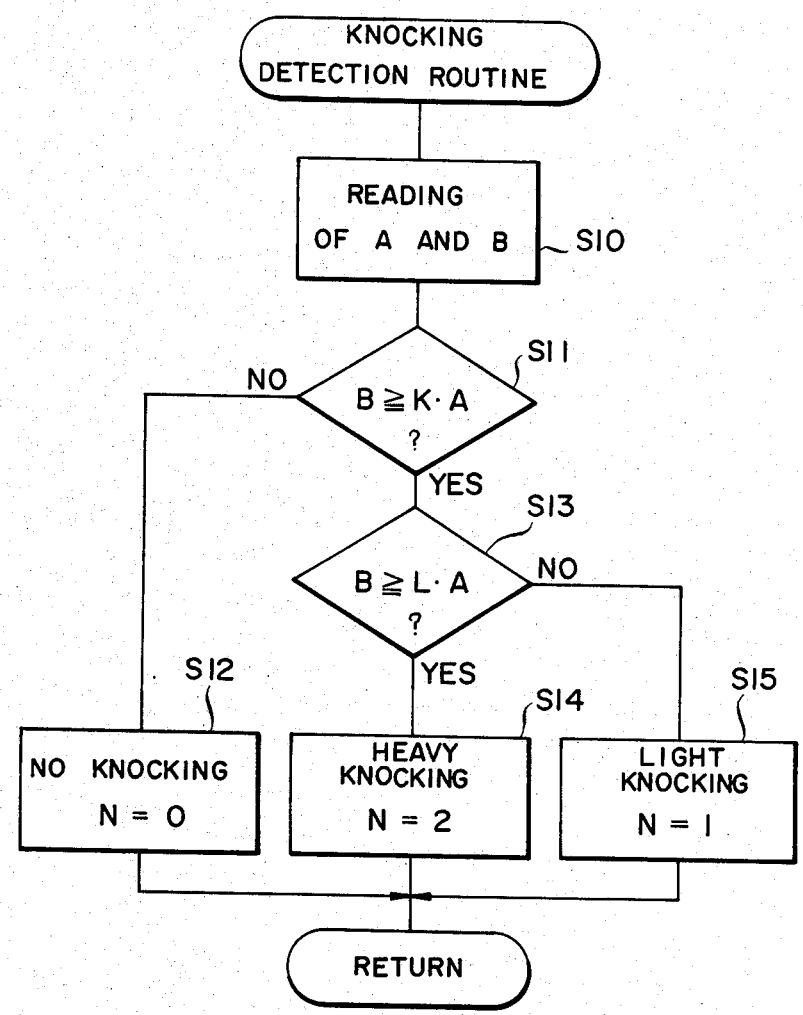
FIG. 7 is one example of a flow chart showing a knocking detection routine.

FIG. 7 shows a knocking detection routine which is programmed in the ROM 41 and used in order that a occurrence of knocking and a magnitude thereof are determined in accordance with the outputs from the integral circuit 54 and the gate circuit 55A. Upon starting this program, a step S10 is firstly carried out where the output of the integral circuit 54 and the output of the peak-hold circuit 55 through the gate circuit 55A are taken in synchronism with the rotational angle of the crank shaft. More specifically, referring to FIG. 5, (b), (d), the output "A" of the integral circuit 54 is taken in at the top dead center of the crank shaft and the output "B" of the gate circuit 55A is taken in at 90° (CA) after the top dead center.

Subsequently, the process proceeds to a step S11 where determination is made as to whether "B" is (K×"A") or greater. K is a constant number and contributes to compensation for different amplification rates of the integral circuit 54, peak-hold circuit 55 and gate circuit 55A. In this embodiment, K is multiplied by "A" resulting in a threshold level (K×"A") as a first reference level of the knocking intensity which is compared with "B". As understood from FIG. 5, the output of the integral circuit 54 at the top dead center of the crank shaft is referred to as the above-mentioned value "A" indicating vibration of the engine 13 other than that caused by knocking or detonation of the engine 13. This is because it has been known that knocking hardly takes place at the top dead center of the crank shaft. Accordingly, when those output "B" of the knocking sensor 32 which is held by the peak-hold circuit 55 between 15° (CA) and 90° (CA), is equal to the threshold level (K×"A") or greater, it is determined that the knocking takes place.

If the decision in the step S11 is negative, the process goes to a step S12 where N is set to be "0" indicating no occurrence of knocking. If a decision in the step S11 is affirmative, the process goes to a step S13 where the magnitude of the knocking is determined by using (L×"A") as a second reference level of the knocking intensity, in which L is greater than K. If the output "B" of the knocking sensor 32 is so great that the output "B" is equal to (L×"A") or greater, it is determined in the step S13 that a considerable great vibration in the gasoline engine 13 occurs, i.e., a heavy knocking takes place and in turn the process goes to a step S14 where N is set to be "2". If the decision of the step S13 is negative, it is determined that a light knocking takes place and in turn the process goes to a step S15 where N is set to be "1".

Fuel Discrimination Routine (1)

Figure 8:
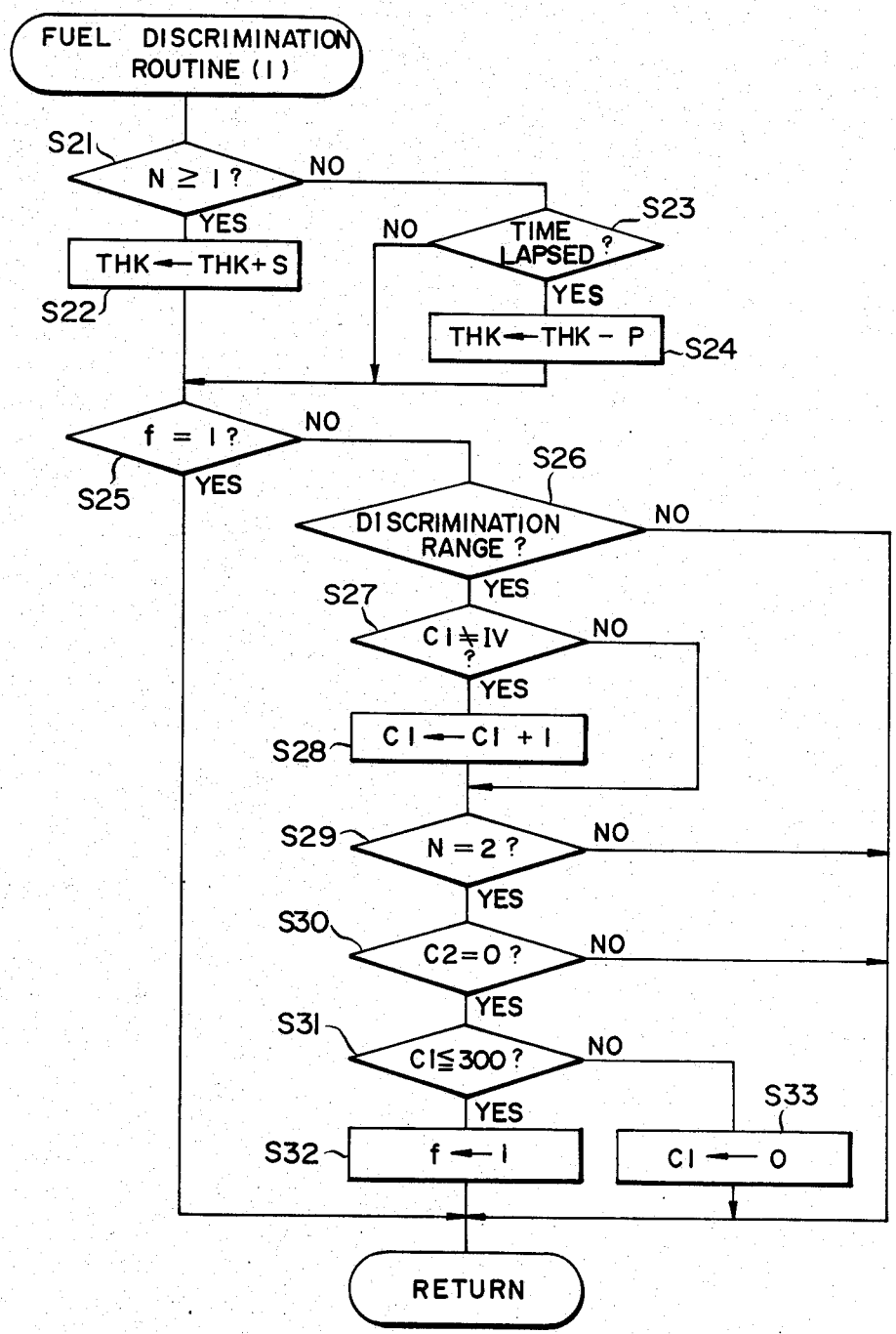
FIGS. 8 and 11 are two example of flow charts showing a fuel discrimination routine.

FIG. 8 shows one example of a fuel discrimination routine wherein discrimination is made as to whether the octane number of the gasoline in the fuel tank is less than the allowable octane number. Upon starting this routine at every 120° (CA), the process goes to a step S21 where determination is made as to whether N is "1" or more, i.e., knocking in the engine takes place or not. If yes, a predetermined value S is added to the correction value THK for retardation of the ignition timing and the result of this addition is set to be the new correction value THK causing the ignition timing to be retarded. If no in the step S21, the process goes to a step S23 where determination is made as to whether a predetermined period of time is elapsed after a previous determination of the knocking or not. If decision in the step S23 is affirmative, the process goes to a step S24 where the correction value THK is subtracted by a predetermined value P and the result of this subtraction is set to be the new correction value THK.

In a step S25 determination is made as to whether the flag f is "1" or not. As described above, the flag f is set to be "1" when it is determined that the low-octane gasoline is used. Once the flag f has been set to be "1", the sequential procedures of step S26-S32 are skipped over and this routine is terminated. As described above, the flag is reset to be "0" in response to turning on of the key switch 34. The flag f, therefore, is kept at "0" until it is determined that the low-octane gasoline is used through the steps S26-S32.

In the step S26, determination is made as to whether or not the correction value THK is within a discrimination range AR in which discrimination is made as to whether the type of gasoline to be supplied to the fuel tank is of high-octane gasoline or low-octane gasoline. According to this embodiment, the discrimination range AR is set as follows:

$$THKmx - 1° (CA) \leq AR \leq THKmx$$

where, THKmx is the maximum value of the correction value THK. It should be noted that it is preferable to set the discrimination range AR in adjacent to the maximum value THKmx of the corection value.

Figure 9:
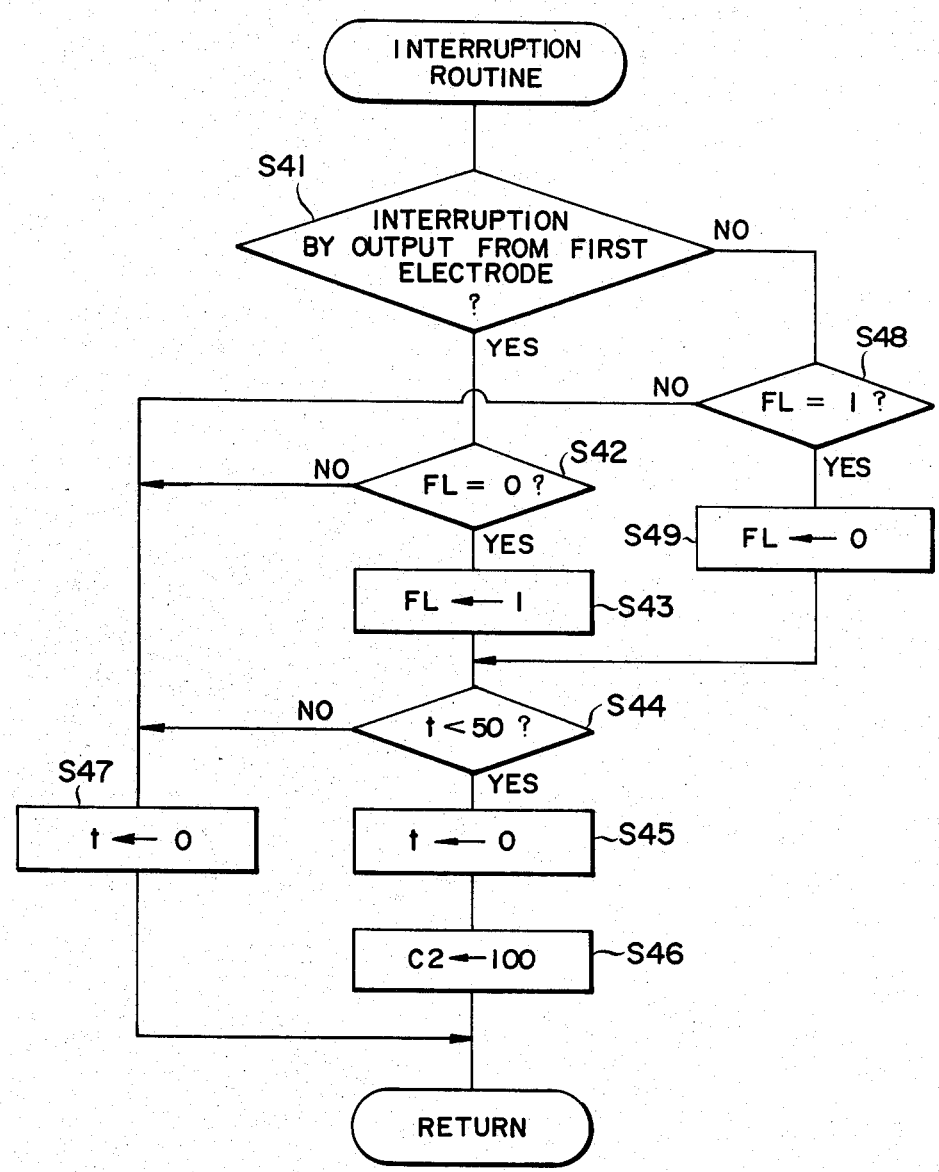
FIG. 9 is one example of a flow chart showing a detection of a rapid acceleration of the engine.
Figure 10:
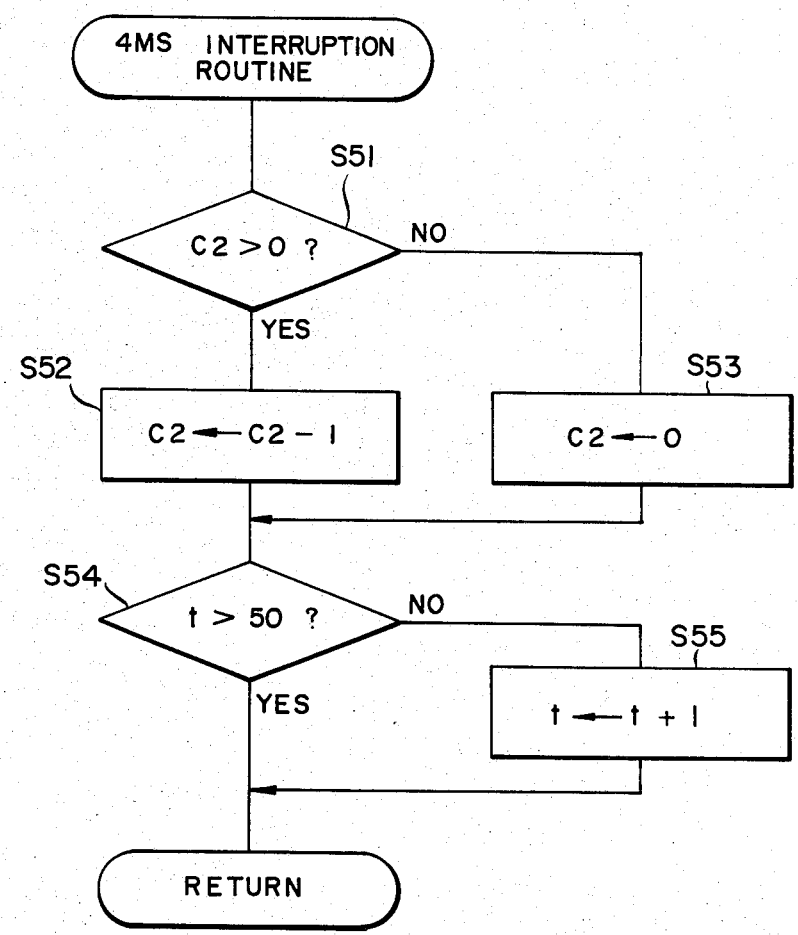
FIG. 10 is one example of a flow chart showing an increase or decrease of counters shown in FIG. 8.

If the decision in the step S26 is affirmative, the process goes to the step S27 where determination is made as to whether a content C1 of a first counter is an initial value IV or not. When the process goes to the step S27 for the first time, the decision in the step S27 is necessarily negative because the first counter is initialized so that the content C1 thereof is set to be the initial value IV at the step S1 shown in FIG. 6. Therefore the process goes to the step S29. In the step S29, determination is made as to whether N is "2" or not, i.e., the heavy knocking has occurred or not. If the decision in the step S29 is affirmative, the process goes to a step S30 where determination is made whether a content C2 of a second counter is equal to zero or not. The second counter measures the time lapsed after a rapid acceleration is detected in accordance with a process as shown in FIGS. 9 and 10 described hereinafter. The content C2 of the second counter is adapted to become "0" when 400 (ms) is lapsed. If the decision in the step S30 is negative, subsequent steps S31-S33 are skipped over and in turn this program is terminated. In short, no discrimination of gasoline is carried out during the rapid acceleration.

If the decision in the step S30 is affirmative, the process goes to a step S31 where determination is made as to whether the content C1 of the first counter is equal to a reference frequency of occurrence of the heavy knocking or less, e.g., "300" or less. Since the counter C1 is increased by "1" at every ignition, "300" in the step S31 means "300" times of ignitions. When the process goes to the step S31 for the first time, the decision in the step S31 is necessarily negative because the initial value IV is set to be greater than 300. Therefore, the process goes to the step S33 where the content C1 of the first counter is set to be "0". If the decision in the step S27 is affirmative, the process goes to the step S28 where "1" is added to the content C1 of the first counter and the result of the addition is stored as the new content C1 of the first counter. Thereafter the process goes to the step S29. The decision in the step S31 is affirmative, the flag f is set to be "1". The decision in the step S26 is negative, the steps S27-S33 are skipped over and in turn this program is terminated.

In short, when it is determined in the step S29 that the heavy knocking occurs for the first time, it is determined in the step S30 that the predetermined time is lapsed after detection of the rapid acceleration, a negative answer is obtained in the step S31, the content C1 of the first counter is set to be zero in the step S33 and then the first counter is started to count the number of ignitions. The content C1 of the first counter is increased by "1" in response to starting of this program at every 120° (CA) in the step S28. When the subsequent decision in the step S29 is made that the heavy knocking ocurs for the second time and such decision in the step S29 is made after the predetermined time is lapsed after the rapid acceleration is detected, determination is made as to whether the content C1 of the first counter is 300 or less in order that the type of gasoline is discriminated. The content C1 of the first counter being equal to 300 or less represents that the heavy knocking has been taken place frequently, i.e., the low-octane gasoline is mixed into the high-octane gasoline to a certain extent or the fuel tank is filled with the low-octane gasoline. Accordingly, the flag f is set to be "1" in the step S32.

It should be noted that different values of the reference frequency of occurrence of the heavy knocking should be selected instead of "300" mentioned above depending on specifications of the gasoline engine and the knocking sensor to be used as well as different factors relating to the motor vehicle. Although the ignition and the fuel injection are automatically controlled in accordance with the result of discrimination of fuel to be used in the above-mentioned embodiment, an audible or a visible output of the result of discrimination may be generated so that the driver selects the ignition and fuel injection control corresponding to the type of fuel thus discriminated.

Further, a timer may be used to measure a time interval between successive heavy knockings in place of usage of the counter counting the number of the ignitions between the successive heavy knockings. Furthermore, in the step S26 determination may be made as to whether the correction value THK is equal to the maximum valve THKmx thereof. The type of fuel may be discriminated by counting the number of occurrences of the heavy knockings.

Acceleration Determination Routine

Explanation will be given of determination of acceleration and measurement of a lapsed time after detection of a rapid acceleration referring to FIGS. 9 and 10.

A routine shown in FIG. 9 is adapted to be started in response to each trailing edge of signals from the first and second electrodes of the sensor 4. Determination is made as to whether the routine has been started in response to the signal from the first electrode of the sensor 4. If yes, determination is made as to whether a flag FL is zero or not in a step S42. If decision in the step S42 is affirmative, process goes to a step S43 where the flag FL is set. If decision in the step S42 is negative, process goes to a step S47 where a content t of a third counter, which is incremented by one at every 4 ms through a "4 ms interruption routine", is set to be "0". If determination is made that the routine of FIG. 9 is started in response to the signal from the second electrode, process goes to a step S48 where determination is made whether the flag FL is "1" or not. If decision of the step S48 is affirmative, the flag FL is reset to be zero in a step S49. If no in the step S48, process goes to the step S47 where the content t of the third counter is reset to be zero.

In a step S44, determination is made as to whether the content t of the third counter is less than 50 (200 m sec). If decision in the step S44 is affirmative, process goes to a step S45 where the content t is set to be "0" and in turn a step S46 is carried out where the content C2 of the second counter is set to be "100" and the second counter is started to count downwardly.

In short, the rapid acceleration is determined when it is determined that a time interval between the signal from the first electrode and the signal from the second electrode is less than 200 m sec, so that the content C2 of the second counter is set to be "100" in order that the second counter is started to count downwardly.

FIG. 10 shows the "4 ms interruption routine" though which the content C2 of the second counter is decremented by one and the content t of the third counter is incremented by one at every 4 m sec. A step S51 is firstly carried out where determination is made as to whether the content C2 of the second counter is greater than zero or not. If decision of the step S51 is affirmative, process goes to a step S52 where "1" is subtracted from the content C2 of the second counter and the result of the subtraction becomes a new content C2. If decision of the step S51 is negative, a step S53 is carried out where the content C2 of the second counter is set to be "0". Subsequently, process proceeds to a step S54 in which determination is made as to whether the content t of the third counter is greater than "50" and if yes, this routine is terminated. If no, in the step S54, process goes to a step S55 where "1" is added to the content t of the third counter.

Alternatively, change of the open degree of the throttle valve 3 or change of a pressure of the intake air pipe is used in order that determination is made as to whether rapid acceleration takes place.

Fuel Discrimination Routine (2)

Figure 11:
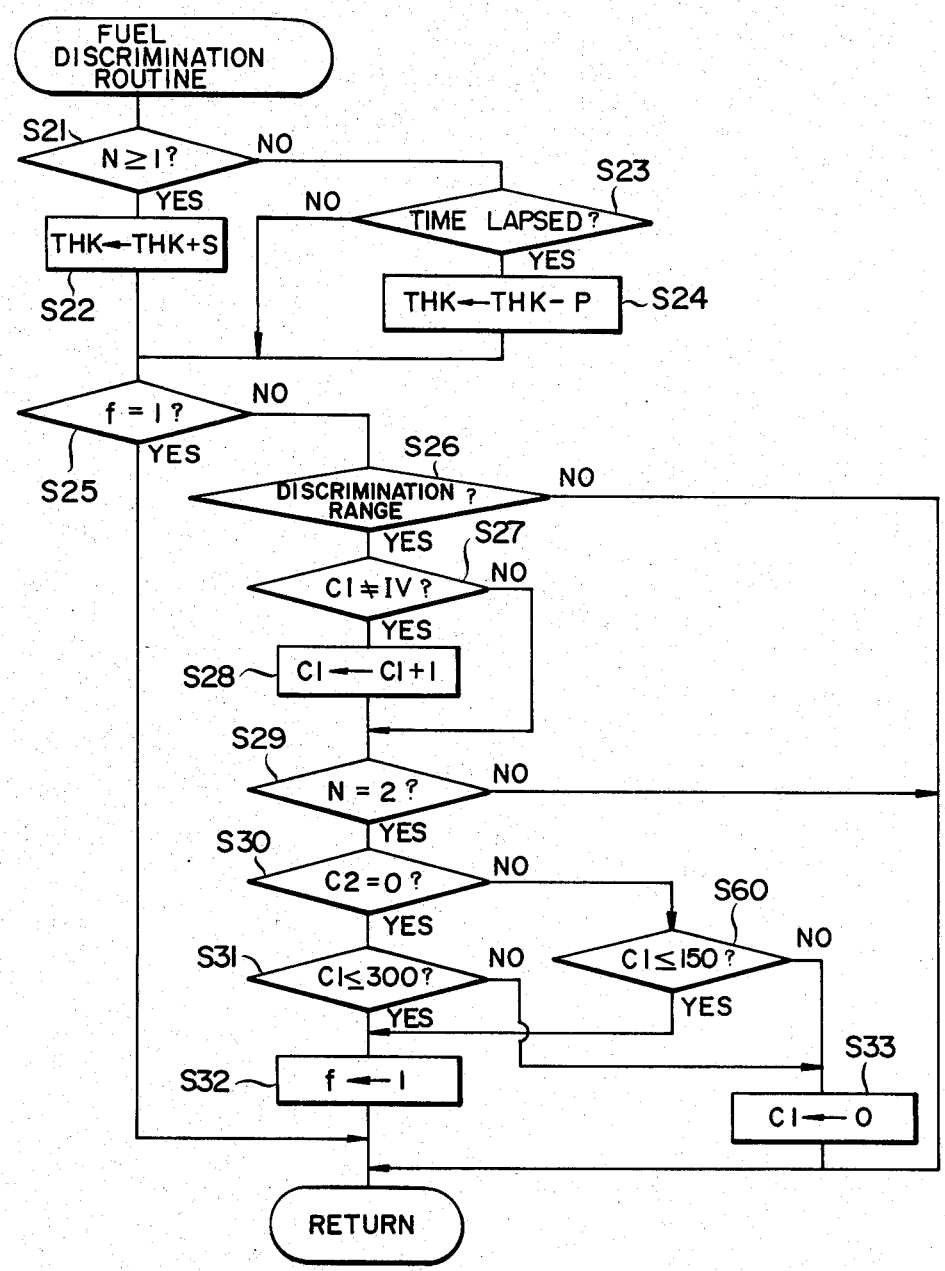

Another embodiment of discrimination of the type of fuel will be explained hereunder referring to FIG. 11.

In this embodiment, fuel discrimination is carried out even if the rapid acceleration is detected and a reference frequency of occurrence of the heavy knocking, which is compared with the number of ignitions between two detections of heavy knockings, is set to be "150" instead of "300". This prevents an erroneous discrimination of the type of fuel.

If the step S30 is determined to be negative, i.e., it is determined that the predetermined time is not lapsed after the rapid acceleration, process proceeds to a step S60 in which the content C1 of the first counter is compared with the reference value "150" for rapid acceleration If the content C1 of the first counter is equal to 150 or less, process proceeds to the step S32 in which the flag f is set to be "1" and if the content C1 is greater than 150, the content C1 is set to be "0" in the step S33. If decision of the step S30 is affirmative, i.e., it is determined that the predetermined time is lapsed after the rapid acceleration, the content C1 is compared with a reference value "300" for steady condition of the engine. If the content C1 is equal to "300" or less, process proceeds to the step S32 where the flag f is set to be "1" and if the content C1 is greater than 300, the content C1 is set to be "0" in the step S33.

According to the second embodiment of the fuel discrimination routine, the type of the fuel is correctly discriminated in accordance with detection of the heavy knocking due to usage of low-octane gasoline, because the reference frequency of occurrence of the heavy knocking is changed during rapid acceleration from "300" to "150".

What is claimed is:

1. A method of discriminating an octane number of a fuel for motor vehicle having an electronic ignition timing system wherein a basic ignition advance angle is determined in accordance with an engine operational condition so that the ignition timing is optimum for a predetermined octane number and is corrected so as to be retarded by using a correction value for retardation of the ignition timing when a knocking greater than a first predetermined level is detected, comprising the steps of:
    determining as to whether the correction value is a predetermined discriminating value in vicinity of the maximum value thereof;
    detecting a rapid acceleration of the engine;
    comparing a frequency of occurrence of the knocking greater than a second predetermined level with a reference frequency; and
    discriminating the fuel as to whether the octane number thereof is the predetermined octane number or not in accordance with the frequency of occurrence of knocking greater than the second predetermined level when it is determined that said correction value is equal to said predetermined discriminating value in said determining step and no rapid acceleration is detected in said detecting step; and
    wherein when said rapid acceleration is detected, said discriminating step is skipped over.

2. A method of discriminating an octane number of a fuel according to claim 1, wherein said predetermined octane number is of high-octane number and said predetermined discriminating value of the correction value for retardation of ignition timing is set to be the maximum value thereof.

3. A method of discriminating an octane number of a fuel according to claim 1, wherein said predetermined octane number is of high-octane number and wherein in said determining step determination is made as to whether the correction value for retardation is within a predetermined discriminating range lying in the vicinity of the maximum value thereof.

4. A method of discriminating an octane number of a fuel according to claim 1, wherein said first predetermind knocking level is less than said second predetermined knocking level.

5. A method of discriminating an octane number of a fuel according to claim 1, wherein said discriminating step is skipped over until a predetermined time is lapsed after detection of said rapid acceleration.

6. A method of discriminating an octane number of a fuel for motor vehicle having an electronic ignition timing system wherein a basic ignition advance angle is determined in accordance with an engine operational condition so that the ignition timing is optimum for a predetermined octane number and is corrected so as to be retarded by using a correction value for retardation of the ignition timing when a knocking greater than a first predetermined level is detected, said method comprising the steps of:
    determining as to whether the correction value is a predetermined discriminating value in vicinity of the maximum value thereof;
    detecting a rapid acceleration of the engine;
    setting a reference frequency of occurrence of the knocking greater than a second predetermined level such that a first reference frequency is selected as said reference frequency when no rapid acceleration is detected and a second reference frequency greater than said first reference frequency is selected as said reference frequency when said rapid acceleration is detected;
    comparing a frequency of occurrence of the knocking greater than a second predetermined level with said reference frequency set in said setting step; and discriminating the fuel as to whether the octane number thereof is the predetermined octane number or not in accordance with the result of said comparing step when it is determined that said correction value is equal to said predetermined discriminating value in said determining step.

7. A method of discriminating an octane number of a fuel according to claim 6, wherein said predetermined octane number is of high-octane number and said predetermined discriminating value of the correction value for retardation of ignition timing is set to be the maximum value thereof.

8. A method of discriminating an octane number of a fuel according to claim 6, wherein said predetermined octane number is of high-octane number and wherein in said determining step determination is made as to whether the correction value for retardation is within a predetermined discriminating range lying in vicinity of the maximum value thereof.

9. A method of discriminating an octane number of a fuel according to claim 6, wherein said first predetermined knocking level is less than said second predetermined knocking level.

10. A method of discriminating an octane number of a fuel according to claim 6 wherein said second reference frequency is held during a predetermined time after detection of said rapid acceleration.

* * * * *